(12) United States Patent
Hagiwara et al.

(10) Patent No.: US 10,012,663 B2
(45) Date of Patent: Jul. 3, 2018

(54) AUTOMATIC ANALYZER

(71) Applicant: HITACHI HIGH-TECHNOLOGIES CORPORATION, Tokyo (JP)

(72) Inventors: Takaaki Hagiwara, Tokyo (JP); Toshiharu Suzuki, Tokyo (JP); Hiroki Fujita, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/313,992

(22) PCT Filed: Apr. 22, 2015

(86) PCT No.: PCT/JP2015/062174
§ 371 (c)(1),
(2) Date: Nov. 25, 2016

(87) PCT Pub. No.: WO2015/186446
PCT Pub. Date: Dec. 10, 2015

(65) Prior Publication Data
US 2017/0205435 A1 Jul. 20, 2017

(30) Foreign Application Priority Data
Jun. 3, 2014 (JP) .................. 2014-115273

(51) Int. Cl.
*G01N 35/02* (2006.01)
*G01N 35/00* (2006.01)
(52) U.S. Cl.
CPC ..... *G01N 35/025* (2013.01); *G01N 35/00603* (2013.01); *G01N 35/00663* (2013.01);
(Continued)
(58) Field of Classification Search
CPC . G01N 2035/00891; G01N 2035/0091; G01N 2035/00435
See application file for complete search history.

(56) References Cited

U.S. PATENT DOCUMENTS

2005/0013736 A1 1/2005 McKeever
2005/0175506 A1 8/2005 Matsubara et al.
(Continued)

FOREIGN PATENT DOCUMENTS

JP 06-213902 A 8/1994
JP 09-072911 A 3/1997
(Continued)

OTHER PUBLICATIONS

Machine-generated English translation of JP 2012-132860, Jul. 12, 2012.*
(Continued)

*Primary Examiner* — P. Kathryn Wright
(74) *Attorney, Agent, or Firm* — Mattingly & Malur, PC

(57) ABSTRACT

A display unit displays, on a single screen, a first display area configured from a first area corresponding to the position on a reagent disc at which a reagent container is disposed and a second display area configured from a second area corresponding to the position on a reagent loader at which a reagent container is disposed. A control unit changes the display state of the first area on the basis of whether a reagent container is placed at a position on the reagent disk corresponding to the first area and reagent information for the reagent accommodated in the placed reagent container and changes the display state of the second area on the basis of whether a reagent container is placed at a position on the reagent loader corresponding to the second area and reagent-container-conveyance-state information for the placed reagent container.

11 Claims, 14 Drawing Sheets

(52) U.S. Cl.
CPC ............ *G01N 35/00693* (2013.01); *G01N 2035/00435* (2013.01); *G01N 2035/00673* (2013.01); *G01N 2035/00891* (2013.01)

(56) References Cited

U.S. PATENT DOCUMENTS

| | | |
|---|---|---|
| 2008/0056939 A1 | 3/2008 | Awata et al. |
| 2008/0063570 A1 | 3/2008 | Fujino et al. |
| 2010/0115463 A1 | 5/2010 | Kondou |
| 2012/0301359 A1 | 11/2012 | Kraemer et al. |
| 2016/0146846 A1* | 5/2016 | Fujita ............... G01N 35/00663 422/67 |

FOREIGN PATENT DOCUMENTS

| | | |
|---|---|---|
| JP | 2004-028932 A | 1/2004 |
| JP | 2008-058125 A | 3/2008 |
| JP | 2008-070115 A | 3/2008 |
| JP | 2012-132860 A | 7/2012 |
| JP | 2012-141162 A | 7/2012 |
| JP | 2012-189611 A | 10/2012 |
| WO | WO-2015005356 A1 * | 1/2015 |

OTHER PUBLICATIONS

International Search Report of PCT/JP2015/062174 dated Jul. 14, 2015.
International Preliminary Report on Patentability received in corresponding International Application No. PCT/JP2015/062174 dated Dec. 8, 2016.
Extended European Search Report received in corresponding European Application No. 15804030.3 dated Feb. 5, 2018.

* cited by examiner

FIG. 6

| REAGENT TYPE / DISPLAY ITEM | ASSAY | PRE | DIL | BLANK, SAP, CELL |
|---|---|---|---|---|
| Position | POSITION No (1-48) | | | |
| Type | ASSAY | PRE | DIL | BLANK, SAP, CELL |
| Name | BLANK SPACE | BLANK SPACE | CONTAINER NAME | CONTAINER NAME |
| Status | STATUS OF RACK PACK (Current,SB1,SB2,...) *MASK STATUS (R.Pack Mask) | STATUS OF RACK PACK (Current,SB1,SB2,...) *MASK STATUS (R.Pack Mask) | STATUS OF RACK PACK (Current,SB1,SB2,...) | ---- |
| R. Pack Lot ID. | MANUFACTURING LOT OF REAGENT RACK PACK | | | |
| R. Pack Sequence No. | MANUFACTURING SEQUENCE NO. OF REAGENT RACK PACK | | | |
| Exp. Date | REAGENT EXPIRATION DATE | REAGENT EXPIRATION DATE | REAGENT EXPIRATION DATE | REAGENT EXPIRATION DATE |
| Remaining Tests | VALIDITY TEST | VALIDITY TEST | ---- | VALIDITY TEST |
| Remaining Volume | ---- | ---- | AVAILABLE REMAINING VOLUME | ---- |
| First Registration Date And Time | FIRST REGISTRATION DATE AND TIME | | | |

FIG. 7

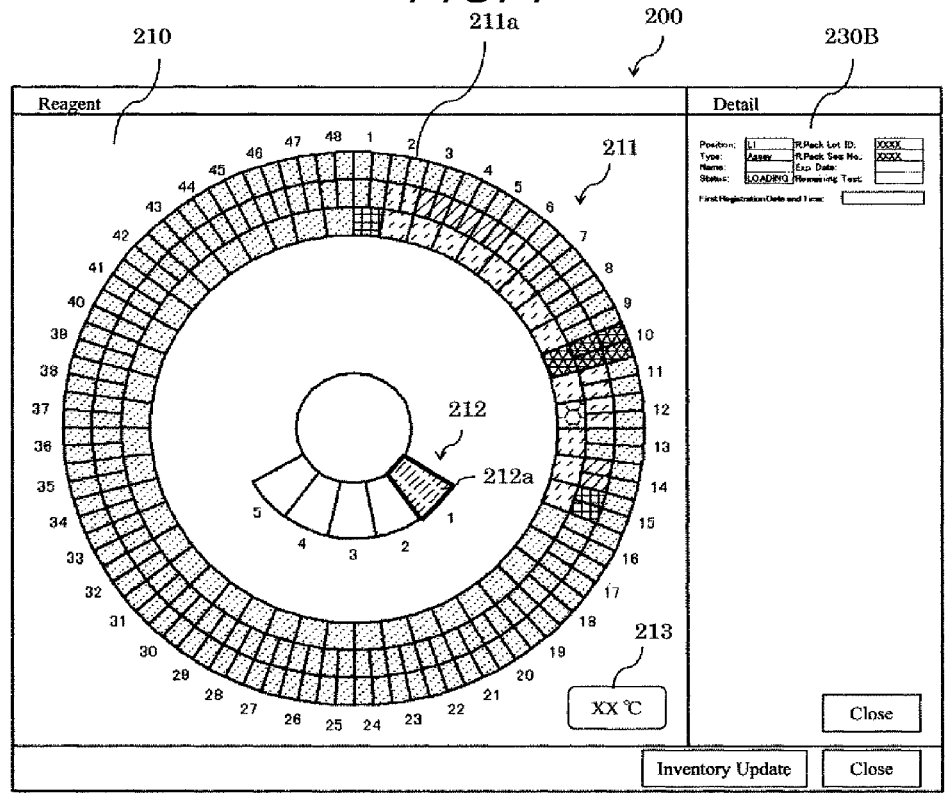

FIG. 8

| REAGENT LOADER DISPLAY ITEM | Loading | Unloading | Auto Closing (Reagent Loader) | Unknown UNKNOWN REAGENT |
|---|---|---|---|---|
| Position | REAGENT POSITION No (L1-L5) | | | |
| Type | ASSAY/PRE/DIL/BLANK/SAP/CELL | | BLANK SPACE | |
| Name | ASSAY/PRE · BLANK SPACE DIL/BLANK/SAP/CELL · CONTAINER NAME | | ????? | |
| Status | LOADING | UNLOADING | A.CLOSE | UNKNWON |
| R. Pack Lot No. | MANUFACTURING LOT OF REAGENT RACK PACK | | BLANK SPACE | |
| R. Pack Sequence No. | MANUFACTURING SEQUENCE NO. OF REAGENT RACK PACK | | BLANK SPACE | |
| Exp. Date | BLANK SPACE | | BLANK SPACE | |
| Remaining Tests | BLANK SPACE | | BLANK SPACE | |
| Remaining Volume | BLANK SPACE | | BLANK SPACE | |
| First Registration Date And Time | BLANK SPACE | | BLANK SPACE | |

FIG. 9

```
                                                        230B
                                                         /
┌─────────────────────────────────────────────────────────┐
│ Detail                                                  │
├─────────────────────────────────────────────────────────┤
│                                                         │
│   Position:  [L1    ]  R.Pack Lot ID:    [XXXX    ]     │
│   Type:      [Assay ]  R.Pack Seq No.:   [XXXX    ]     │
│   Name:      [      ]  Exp. Date:        [        ]     │
│   Status:    [LOADING] Remaining Test:   [        ]     │
│                                                         │
│   First Registration Date and Time:  [              ]   │
│                                                         │
│                                                         │
│                                                         │
│                                              ┌───────┐  │
│                                              │ Close │  │
│                                              └───────┘  │
└─────────────────────────────────────────────────────────┘
```

Detail

| Position: | L2 | R.Pack Lot ID: | XXXX |
| Type: | PRE | R.Pack Seq No.: | XXXX |
| Name: | | Exp. Date: | |
| Status: | LOADING | Remaining Test: | |

First Registration Date and Time:

Close

| Detail | | | |
|---|---|---|---|
| Position: | L5 | R.Pack Lot ID: | XXXX |
| Type: | DIL | R.Pack Seq No.: | XXXX |
| Name: | Dil Uni | Exp. Date: | |
| Status: | UNLOADING | Remaining Test: | |

First Registration Date and Time:

Close

| Detail | | | |
|---|---|---|---|
| Position: | L5 | R.Pack Lot ID: | |
| Type: | | R.Pack Seq No.: | |
| Name: | ????? | Exp. Date: | |
| Status: | A.CLOSE | Remaining Test: | |

First Registration Date and Time:

Close

FIG. 13

Detail — 230B

Position: L5
Type:
Name: ?????
Status: UNKNOWN

R.Pack Lot ID:
R.Pack Seq No.:
Exp. Date:
Remaining Test:

First Registration Date and Time:

Close

FIG. 15

AREA 211a

| POSITION (AREA) / STATUS COLOR | INNER PERIPHERY (P1) REGENT | MIDDLE PERIPHERY (P2) CALIBRATION | OUTER PERIPHERY (P3) QC |
|---|---|---|---|
| C1 | IN USE (Active) | VALID RESULT (Valid) | NO QC ERROR (Valid) |
| C2 | NUMBER OF VALIDITY TESTS < PREPARATION LEVEL (*1) (Preparation) | — | — |
| C3 | NUMBER OF VALIDITY TESTS < WARNING LEVEL (Warning) | RECOMMENDATION OR REQUEST (Requested) | RECOMMENDATION OR REQUEST (Requested) |
| C4 | INVALID REAGENT (Caution) | NO VALID RESULT (Failed) | QC ERROR (*2) (Violated) |
| C5 | STAND BY (Stand By) | — | NO QC RESULT (N.A) |
| C6 | USED UP (REMAINING REAGENT VOLUME 0) (Used Up) | .... | .... |
| C7 | EMPTY POSITION (Free Pos.) | EMPTY POSITION OR OTHER THAN ASSAY REAGENT (Free Pos.) | EMPTY POSITION OR OTHER THAN ASSAY REAGENT (Free Pos.) |
| C8 | REGENT EXPIRED (Invalidity) | | |

— : NON-EXISTING CONDITION
( ) : LEGEND DISPLAY CHARACTERS
*1 : DETERMINATION AVAILABLE WHEN A PREDETERMINED FUNCTION IS IN ON STATE
*2 : DETERMINATION RESULT IS NOTIFIED FROM HIGH-ORDER SYSTEM

FIG. 16

AREA 212a

| STATUS COLOR | STATUS OF REAGENT LOADER POSITION | LED (*1) |
|---|---|---|
| C2 | ·Loading (UNTIL MOVING TO REAGENT DISC)<br>(Preparation) | C11 |
| C3 | ·Unloading: RE-REGISTRATION AVAILABLE STATUS BY Foam/Film DETECTION, ETC.<br>·TEMPORARILY Loading UNAVAILABLE: RE-REGISTRATION AVAILABLE STATUS BY NO ANALYSIS PARAMETERS WHEN Loading, NO EMPTY POSITION IN REAGENT DISC, REAGENT REVERSE INSTALLATION, ETC.<br>(Warning) | C12 |
| C4 | ·Unloading: RE-REGISTRATION UNAVAILABLE STATUS BY REMAINING VOLUME 0, EXPIRED REAGENT, ETC.<br>·Loading UNAVAILABLE: RE-REGISTRATION UNAVAILABLE STATUS BY REMAINING VOLUME 0 WHEN Loading, EXPIRED DATE, ETC.<br>·Auto-Closing STATUS<br>·UNKNOWN REAGENT STATUS<br>(Caution) | C13 |
| C5 | Unloading: Manual Unloading<br>(Stand-by) | C14 |
| C6 | EMPTY POSITION<br>(Free Pos.) | OFF |

AUTOMATIC ANALYZER

TECHNICAL FIELD

The present invention relates to an automatic analyzer performing qualitative/quantitative analyses of a biological sample such as blood and urine.

BACKGROUND ART

An automatic analyzer capable of automatically exchanging reagents during analyzing has been known (see PTL 1, for example). The automatic analyzer disclosed in PTL 1 includes a reagent disc mechanism (reagent container storage portion) having a driving disc and a fixed disc which is arranged to be concentrically fixed with respect to the driving disc, a loading system (reagent loader) which forms a part of the periphery of the fixed disc and has a reagent placing unit capable of placing a plurality of reagent containers, and a reagent container moving unit which moves the reagent containers between the loading system and a reagent driving disc.

CITATION LIST

Patent Literature

PTL 1: JP 2012-189611 A

SUMMARY OF INVENTION

Technical Problem

In the technology disclosed in PTL 1, carrying a plurality of reagent containers into the reagent disc or carrying a plurality of reagent containers from the reagent disc can be performed by the reagent loader. In this case, a time at which carrying-in or carrying-out of the reagent containers is performed is decided by a user.

To effectively perform the exchange of the reagents, it is preferable that the reagent loader is operated in a state where reagent containers to be carried out be placed at every slots of the reagent loader.

However, in the technology of the related art, it is not possible to grasp the status of reagent containers placed at a reagent loader and the status of reagent containers placed at a reagent disc at the same time. Therefore, there is a problem in that the reagent exchange cannot be performed effectively.

An object of the invention is to provide an automatic analyzer capable of effectively exchanging reagents by using a reagent loader which carries a plurality of reagent containers into a reagent container storage portion or carries a plurality of reagent containers from the reagent container storage portion.

Solution to Problem

In order to achieve the object, the present invention provides an automatic analyzer, including: a reagent container storage portion which stores a plurality of reagent containers; a memory unit which memorizes reagent information showing the information on a reagent accommodated in the reagent container; a reagent loader which has a plurality of slots into which the reagent containers are inserted and conveys the reagent container between the outside and the reagent container storage portion so as to carry the reagent container into the reagent container storage portion and carry the reagent container from the reagent container storage portion; a display unit which displays a first display area configured by a first area corresponding to a position on the reagent container storage portion at which the reagent container is placed and a second display area configured by a second area corresponding to a position on the reagent loader at which the reagent container is placed on a single screen; and a control unit which changes the display state of the first area on the basis of whether the reagent container is placed at a position on the reagent container storage portion corresponding to the first area and the reagent information of the reagent accommodated in the placed reagent container and changes the display state of the second area on the basis of whether the reagent container is placed at a position on the reagent loader corresponding to the second area and conveyance-state information showing the conveyance state of the placed reagent container, wherein the conveyance-state information includes at least a loading state which is the state where the reagent container in the middle of being carried into the reagent container storage portion is disposed at the slot and an unloading state which is the state where the reagent container in the middle of being carried out from the reagent container storage portion is disposed at the slot.

Advantageous Effects of Invention

According to the invention, it is possible to effectively perform the exchange of reagents by using a reagent loader which carries a plurality of reagent containers into a reagent container storage portion or carries a plurality of reagent containers from the reagent container storage portion. Problems, configurations, and effects other than those described above will become apparent from the following description of an embodiment.

BRIEF DESCRIPTION OF DRAWINGS

FIG. 6 is a view illustrating display items of a Detail window illustrated in FIG. 5.

FIG. 7 is a view for describing the Detail window which is displayed when an area 212a of a loader position display area of the Reagent window is selected.

FIG. 8 is a view illustrating display items of the Detail window illustrated in FIG. 7.

FIG. 9 is a view illustrating display items of the Detail window when the reagent type of a reagent container placed at a position corresponding to a first area 212a of the loader position display area of the Reagent window illustrated in FIG. 7 is "ASSAY".

FIG. 10 is a view illustrating display items of the Detail window when the reagent type of a reagent container placed at a position corresponding to a second area 212a of the loader position display area of the Reagent window illustrated in FIG. 7 is "PRE".

FIG. 11 is a view illustrating display items of the Detail window when the reagent type of a reagent container placed at a position corresponding to a fifth area 212a of the loader position display area of the Reagent window illustrated in FIG. 7 is "DIL".

FIG. 12 is a view illustrating display items of the Detail window when a reagent loader is automatically closed.

FIG. 13 is a view illustrating display items of the Detail window when the reagent type is unknown.

FIG. 15 is a view illustrating an example of colors used for the area 211a of the disc position display area.

FIG. 16 is a view illustrating an example of colors used for the area 212a of the loader position display area.

DESCRIPTION OF EMBODIMENTS

Figure 1:
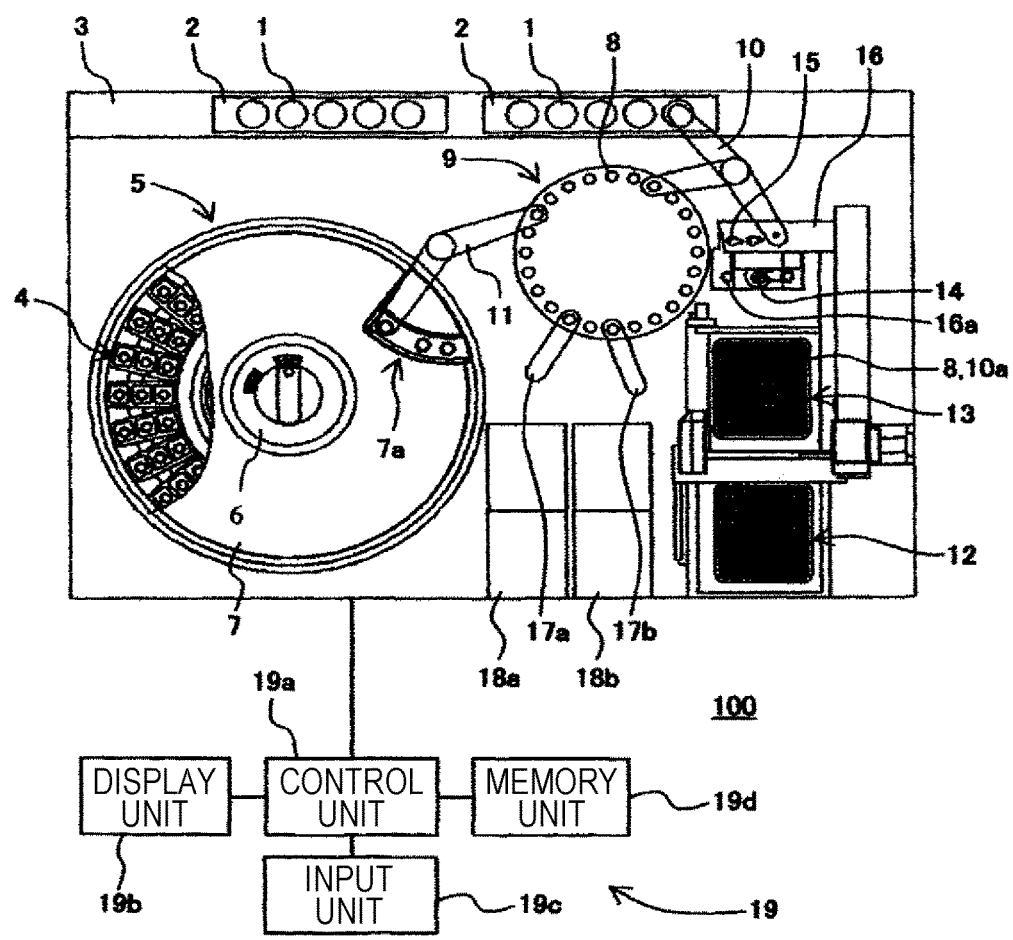
FIG. 1 is a configuration view of an automatic analyzer of an embodiment of the invention.

Hereinafter, the configuration and operation of an automatic analyzer 100 of an embodiment of the invention will be described with reference to FIGS. 1 to 16. The automatic analyzer 100 is an analyzer in which, for example, analyses of different types such as biochemistry and immune are performed by a single system. In addition, in FIGS. 1 to 16, the same reference numerals and characters are given to the same parts.

First, the entire configuration of the automatic analyzer 100 of the embodiment of the invention will be described with reference to FIG. 1. FIG. 1 is a configuration view of the automatic analyzer 100 of the embodiment of the invention.

The automatic analyzer 100 includes a sample container rack 2, a rack conveyance line 3, a reagent disc 5, a reagent loader 6, an incubator disc 9, a sample dispensing nozzle 10, a reagent dispensing nozzle 11, a reaction container/sample dispensing chip accommodation portion 13, a replacement/replenishment reaction container/sample dispensing chip accommodation portion 12, a reaction container agitating mechanism 14, a waste hole 15, a conveyance mechanism 16, a nozzle 17 (17a and 17b), a detection unit 18 (18a and 18b), and a control device 19.

The sample container rack 2 accommodates a plurality of sample containers 1 in which a biological sample (hereinafter, referred to as a sample) such as blood and urine is accommodated. The rack conveyance line 3 conveys the sample container rack 2.

The reagent disc 5 (the reagent container storage portion) is covered by a reagent disc cover 7. The reagent disc 5 accommodates a plurality of reagent containers 4 in which various reagents used for analyzing a sample are accommodated and keeps them warm (cold). In other words, the reagent disc 5 stores the reagent containers 4 (the reagent rack packs). A reagent container opening device (not illustrated) is provided in the reagent disc 5 to perform opening of the reagent container 4. The type of the reagent disc 5 is not limited to the disc type and may be the serial type in which the reagent containers 4 are arranged in one or more rows.

The reagent loader 6 is provided in the inner peripheral portion of the reagent disc 5. The reagent loader 6 carries the reagent container 4 from the outside to the reagent disc 5 when the reagent container 4 is placed and carries the reagent container 4 from the reagent disc 5 to the outside when the reagent container 4 is taken out. The detail of the configuration of the reagent loader 6 will be described below with reference to FIG. 2.

The incubator disc 9 accommodates a plurality of reaction containers 8 for mixing samples and reagents. The sample dispensing nozzle 10 dispenses samples from the sample container 1 into the reaction container 8 of the incubator disc 9 by rotation driving or vertical driving, and a suction/discharge operation.

The reagent dispensing nozzle 11 dispenses reagents from the reagent container 4 into the reaction container 8 of the incubator disc 9 by rotation driving or vertical driving, and a suction/discharge operation through a reagent disc cover opening portion 7a provided in the reagent disc cover 7. The reaction container agitating mechanism 14 agitates reaction solution accommodated in the reaction container 8.

The reaction container/sample dispensing chip accommodation portion 13 accommodates a plurality of unused reaction containers 8 or sample dispensing chips 10a. The reaction container/sample dispensing chip accommodation portion 12 stands by for replacement/replenishment. The waste hole 15 is a hole through which the used sample dispensing chip 10a and the used reaction container 8 are wasted.

The conveyance mechanism 16 conveys the sample dispensing chip 10a and the reaction container 8 by grasping them. In detail, the conveyance mechanism 16 is provided to be able to move in the X-axis, Y-axis, and Z-axis directions (not illustrated). The conveyance mechanism 16 conveys the reaction container 8 accommodated in the reaction container/sample dispensing chip accommodation portion 13 to the incubator disc 9, wastes the used reaction container 8 to the waste hole 15, or conveys the unused sample dispensing chip 10a to a chip mounting position 16a.

The nozzles 17a and 17b suck up the reaction solutions mixed in the reaction containers 8 of the incubator disc 9 and respectively send the solutions to detection units 18a and 18b by rotation driving or vertical driving. The detection units 18a and 18b detect specific components by performing detection processes on the reaction solutions which are sucked up and sent by the nozzles 17a and 17b.

The control device 19 controls the entire operations of the automatic analyzer 100. The control device 19 includes a control unit 19a, a display unit 19b, an input unit 19c, and a memory unit 19d. In this case, the memory unit 19d memorizes, for example, reagent information indicating the information on a reagent accommodated in the reagent container 4.

Figure 2:
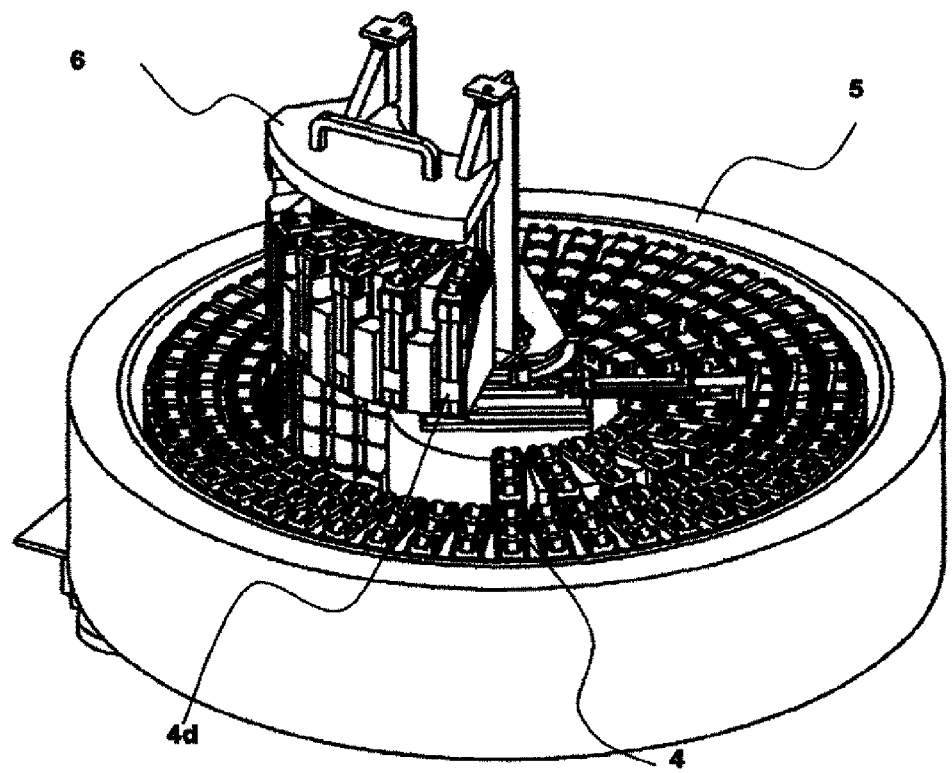
FIG. 2 is a view for describing the configuration of the peripheral portion of a reagent disc used for the automatic analyzer of the embodiment of the invention.

Next, the configuration of the peripheral portion of the reagent disc 5 used for the automatic analyzer 100 of the embodiment of the invention will be described with reference to FIG. 2. FIG. 2 is a view for describing the configuration of the peripheral portion of the reagent disc 5 used for the automatic analyzer 100 of the embodiment of the invention. The reagent disc 5, the reagent loader 6, and the peripheral configurations thereof are illustrated in FIG. 2.

A plurality of reagent containers 4 are installed in the reagent disc 5. The reagent disc 5 includes the reagent loader 6 in the inner peripheral portion (in the vicinity of the center of the reagent disc 5) thereof. The reagent loader 6 has a plurality of slots into which the reagent containers 4 are inserted. In FIG. 2, the reagent loader 6 has a configuration in which five reagent containers 4 can be placed. However, the configuration of the reagent loader 6 is not limited thereto. The reagent loader 6 carries in or out the reagent container 4 between the outside and the reagent disc 5 by being moved in a vertical direction.

A scanning device is provided in the reagent disc 5 to scan an individual identification mark 4d (RFID tag in this embodiment) provided in the reagent container 4 and send the identification information to the control unit 19a of the control device 19. In addition, a bar code label or the like may be used as the individual identification mark 4d of the reagent container 4.

The identification information recorded in the individual identification mark 4d includes a reagent identification number (reagent identification code) for identifying the reagent accommodated in the reagent container 4, the test item name, the lot number, and the sequence number corresponding to the accommodated reagent, and the like.

Figure 3:
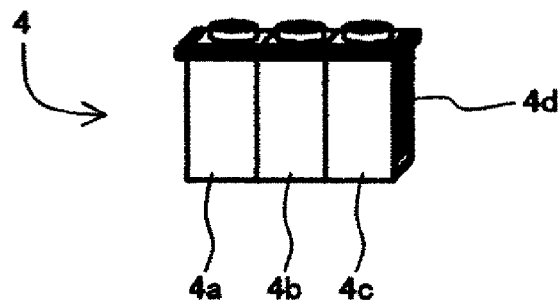
FIG. 3 is a configuration view of a reagent container used for the automatic analyzer of the embodiment of the invention.

Next, the configuration of the reagent container 4 used for the automatic analyzer 100 of the embodiment of the invention will be described with reference to FIG. 3. FIG. 3 is a configuration view of the reagent container 4 used for the automatic analyzer 100 of the embodiment of the invention.

The reagent container 4 is configured by reagent vessels 4a to 4c which accommodate reagents. The reagent containers 4 are mainly classified into a container for accommodating a group of reagents for analyses corresponding to the test item into reagent vessels 4a to 4c, a container for accommodating diluting solution into reagent vessels 4a to 4c, and a container for accommodating reagents for identifying the device status into reagent vessels 4a to 4c.

Figure 4:
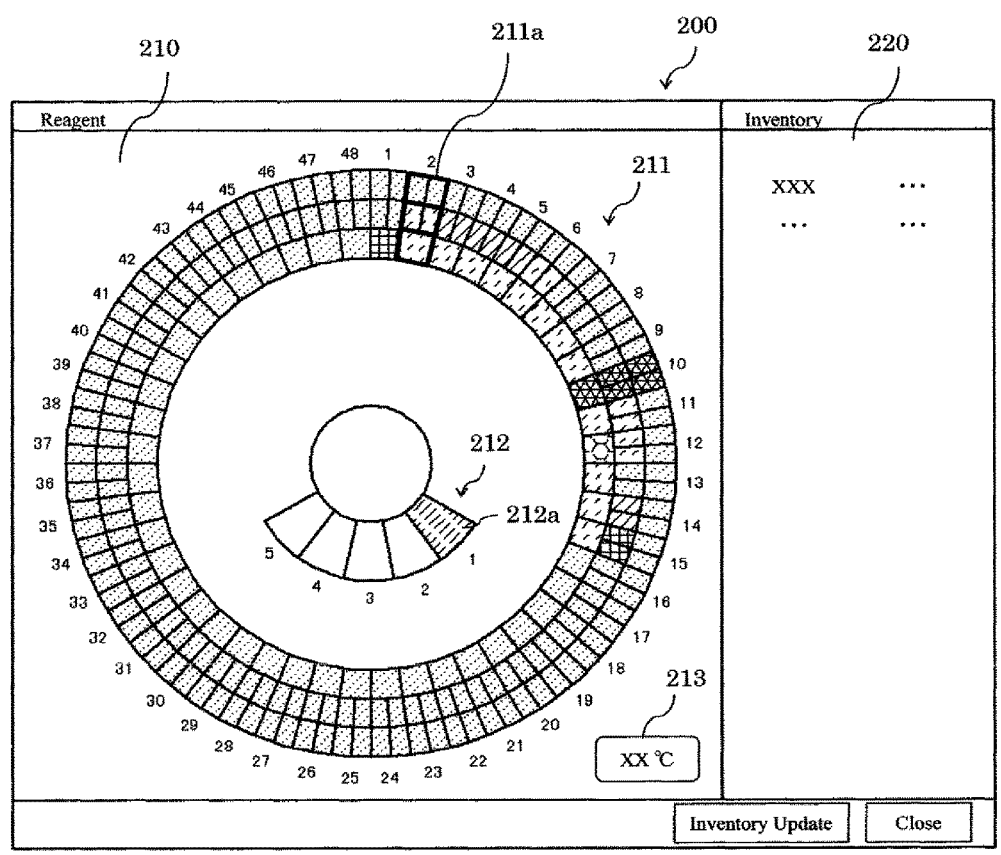
FIG. 4 is a view for describing a screen as a GUI used for the automatic analyzer of the embodiment of the invention.

Next, a screen 200 displayed on the display unit 19b will be described with reference to FIG. 4. FIG. 4 is a view for describing the screen 200 as a GUI used for the automatic analyzer 100 of the embodiment of the invention.

The control unit 19a displays, on the display unit 19b, the screen 200 showing the status of the reagent containers 4 placed at the reagent disc 5 and the reagent loader 6 in response to, for example, the pressing of a predetermined button. Furthermore, when the Inventory Update button of the screen 200 is pressed, the control unit 19a updates the display items of the screen 200. In addition, when the Close button of the screen 200 is pressed, the screen 200 is closed.

The screen 200 includes a Reagent window 210 (area 210) which visually displays the position and status of the reagent container 4 and an Inventory window 220 (area 220) which displays the stock of consumable parts.

The Reagent window 210 includes a disc position display area 211 showing the status of the reagent containers 4 placed at the reagent disc 5, a loader position display area 212 showing the status of the reagent containers 4 placed at the reagent loader 6, and a temperature displaying area 213 displaying the temperature inside the reagent disc 5. Furthermore, a temperature sensor is provided in the reagent disc 5 and sends the measured temperature to the control unit 19a.

The disc position display area 211 is configured by a first area 211a (position) corresponding to the position of the reagent container 4 placed at the reagent disc 5. Furthermore, in the example of FIG. 4, numbers 1 to 48 are respectively assigned to the areas 211a. The detail of the area 211a will be described below with reference to FIG. 14.

The loader position display area 212 is configured by a second area 212a (position) corresponding to the position of the reagent container 4 placed at the slot of the reagent loader 6. Furthermore, in an example of FIG. 4, numbers 1 to 5 are respectively assigned to the areas 212a.

In the embodiment, the statuses of the reagent containers 4 corresponding to the areas 211a and 212a are displayed by the colors of the areas. The meaning of the colors of the areas 211a and 212a will be described below with reference to FIGS. 15 and 16.

Figure 5:
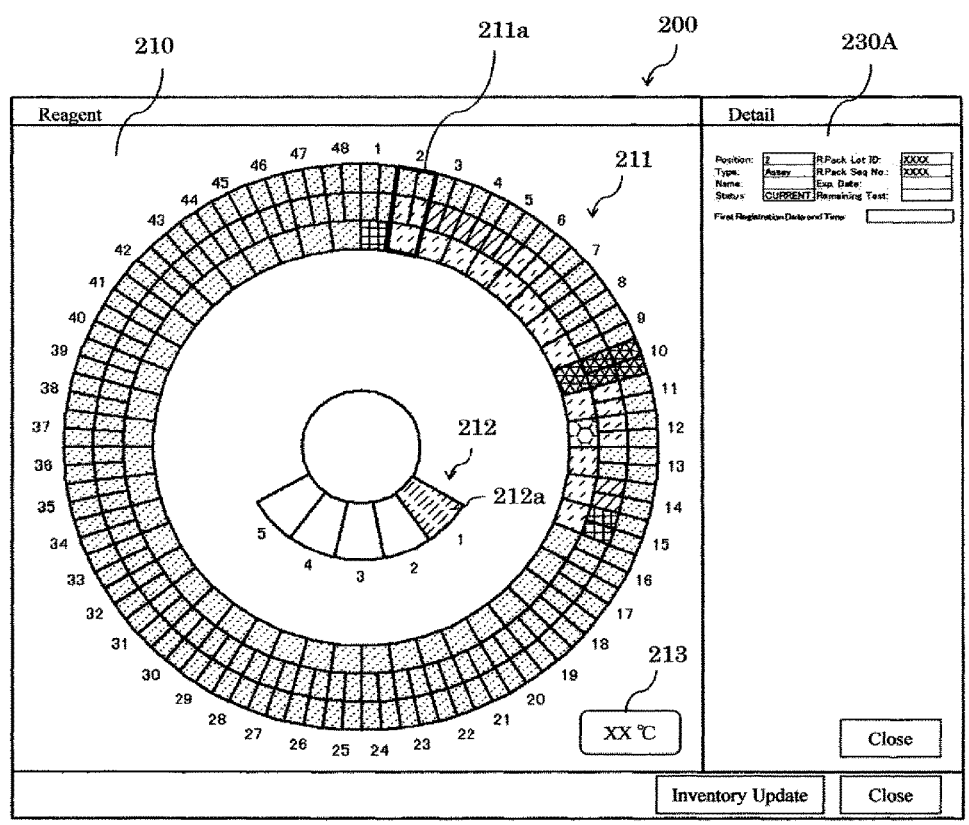
FIG. 5 is a view for describing a Detail window which is displayed when an area 211a of a disc position display area of a Reagent window is selected.

Next, the transition of the screen 200 will be described with reference to FIG. 5. FIG. 5 is a view for describing a Detail window 230A which is displayed when the area 211a of the disc position display area 211 of the Reagent window 210 is selected.

When the input unit 19c receives the information that the area 211a of the number m (m=1, 2, . . . , 48) of the disc position display area 211 is selected (designated), the control unit 19a displays the Detail window 230A (the area 230A) showing the detail of the status of the reagent accommodated in the reagent container 4 placed at a position corresponding to the area 211a of the number m. In addition, in FIG. 5, the control unit 19a displays the Detail window 230A instead of the Inventory window 220, comparing to in the case of FIG. 4.

In the example of FIG. 5, the control unit 19a displays "Position" showing the number of the selected area 211a, "Type" showing the reagent type of the reagent accommodated in the reagent container 4, "Name" showing the name of the reagent container 4, "Status" showing the status of the reagent container 4, an "R. Pack Lot ID" showing the lot number of the reagent container 4, an "R. Seq. Lot ID" showing the product sequence number of the reagent container 4, an "Exp. Date" showing the expiration date of the reagent accommodated in the reagent container 4, "Remaining Test" showing the number of remaining tests (the validity tests) of the reagent accommodated in the reagent container 4, and "First Registration Date and Time" showing the first registration date and time of the reagent container 4 on the Detail window 230A as the detail of the reagent accommodated in the reagent container 4 placed at a position corresponding to the area 211a of the number 2.

The display items of the Detail window 230A are different in accordance with the reagent type ("Type"). FIG. 6 is a view illustrating the display items of the Detail window 230A illustrated in FIG. 5.

The examples of the reagent type ("Type") are an "ASSAY" indicating a reagent for analyzing used for general analyses, "PRE" indicating a reagent for preprocessing, "DIL" indicating diluting solution, and "BLANK", "SAP", and "CELL" indicating reagents for identifying the status of the device.

When the reagent type ("Type") is "DIL", "BLANK", "SAP", or "CELL", the control unit 19a displays the container name of the reagent container 4 on "Name". When the reagent type ("Type") is "ASSAY" or "PRE", the control unit 19a displays a blank space on "Name". When the reagent type ("Type") is "DIL", the control unit 19a adds "Remaining Volume" showing the remaining volume of the reagent to the Detail window 230A as a display item.

There are tests (analyses) using the reagent accommodated in the reagent container 4 of which the reagent type ("Type") is "ASSAY" and the reagent accommodated in another reagent container 4 of which the reagent type is "ASSAY". In this case, the control unit 19a displays a unique combination test name on "Name".

When there are a plurality of reagent containers 4 storing reagents of which the reagent type ("Type") is "ASSAY", "PRE", or "DIL", the control unit 19a displays "Current" on "Status" in relation to the reagent container 4 in use. On the contrary, the control unit 19a displays characters, combining "SB" meaning the standby state and sequential numbers, on "Status" in relation to the unused reagent container 4.

When the reagent container 4 stores a reagent which is used for a test item set to not be able to be measured by a user and of which the reagent type ("Type") is "ASSAY", the control unit 19a masks "Status". This state will be referred to as a reagent-manual-masking state.

Next, the transition of the screen 200 will be described with reference to FIG. 7. FIG. 7 is a view for describing a Detail window 230B which is displayed when the area 212a of the loader position display area 212 of the Reagent window 210 is selected.

When the input unit 19c receives the information that the area 212a of the number n (n=1, 2, . . . , 5) of the loader position display area 212 is selected (designated), the control unit 19a displays the Detail window 230B (the area 230B) showing the detail of the status of the reagent accommodated in the reagent container 4 placed at a position corresponding to the area 212a of the number n.

In the example of FIG. 7, the control unit 19a displays the display items similar to those of the Detail window 230A on the Detail window 230B. However, "Status" shows the status of the reagent container 4 placed at the reagent loader 6. In addition, in the example of FIG. 7, the control unit 19a displays the number of the area 212a, the number being given with the character L" on "Position". The reason for this is to distinguish it from the number of the area 211a of the disc position display area 211.

In this case, the display items of the Detail window 230B differ in accordance with the reagent type ("Type") and the status ("Status") of the reagent container 4 placed at the reagent loader 6. FIG. 8 is a view illustrating the display items of the Detail window 230B illustrated in FIG. 7.

Examples of the status ("Status") of the reagent container 4 placed at the reagent loader 6 are "LOADING", "UNLOADING", "A. CLOSE", and an "UNKNOWN".

In this case, "LOADING" indicates the state until the reagent container 4 is placed at the reagent disc 5 after the reagent loader 6 is moved from the highest position (the position at which a user inserts the reagent container 4 into the slot) to the lowest position. In addition, when there are a plurality of reagent containers 4 storing the reagents of the same reagent type, the priority (the order of use) is not determined on the reagent loader 6.

"UNLOADING" indicates the state until the reagent loader 6 is moved from the lowest position to the highest position after the reagent container 4 is moved from the reagent disc 5 to the reagent loader 6.

"A. CLOSE" indicates the state where the reagent loader 6 is moved to the highest position in response to the operation of a user, and then the reagent loader 6 is temporarily automatically moved (auto closing) to the lowest position when a predetermined time is elapsed. Auto closing is performed to prevent an increase in the temperature inside the reagent disc 5.

"UNKNOWN" indicates the state where, although the control unit 19a detects the presence of the reagent container 4 by the signal from the scanning device, the reagent type cannot be identified due to tag reading failure, hardware errors, or the like.

When the status ("Status") of the reagent container placed at the reagent loader 6 is "LOADING" or "UNLOADING" and the reagent type ("Type") is "ASSAY" or "PRE", the control unit 19a displays a blank space on "Name". On the contrary, when the status ("Status") of the reagent container 4 placed at the reagent loader 6 is "LOADING" or "UNLOADING" and the reagent type ("Type") is "DIL, "BLANK", "SAP", or "CELL", the control unit 19a displays the container name of the reagent container 4 on "Name".

When the status ("Status") of the reagent container 4 placed at the reagent loader 6 is "LOADING" or "UNLOADING", the control unit 19a displays the lot number and the sequence number on "R. Pack Lot ID" and "R. Seq. Lot ID". On the contrary, when the status ("Status") of the reagent container 4 placed at the reagent loader 6 is "LOADING" or "UNLOADING", the control unit 19a displays the blank spaces on "R. Pack Lot ID" and "R. Seq. Lot ID".

In addition, the control unit 19a displays the blank spaces on "Exp. Date", "Remaining Test", "Remaining Volume", and "First Registration Date and Time".

Next, the configuration of the Detail window 230B will be described with reference to FIGS. 9 to 13.

FIG. 9 is a view illustrating the display items of the Detail window 230B when the reagent type of the reagent container 4 placed at the position corresponding to a first area of area 212a of the loader position display area 212 of the Reagent window 210 illustrated in FIG. 7 is "ASSAY". In the example of the FIG. 9, the status ("Status") of the reagent container 4 placed at the reagent loader 6 is "LOADING".

FIG. 10 is a view illustrating the display items of the Detail window 230B when the reagent type of the reagent container 4 placed at the position corresponding to a second area of area 212a of the loader position display area 212 of the Reagent window 210 displayed in FIG. 7 is "PRE". In the example of FIG. 10, the status ("Status") of the reagent container 4 placed at the reagent loader 6 is "LOADING".

FIG. 11 is a view illustrating the display items of the Detail window 230B when the reagent type of the reagent container 4 placed at the position corresponding to a fifth area of area 212a of the loader position display area 212 of the Reagent window 210 illustrated in FIG. is "DIL". In the example of FIG. 11, the status ("Status") of the reagent container 4 placed at the reagent loader 6 is "UNLOADING". Furthermore, in the example of FIG. 11, the control unit 19a displays "Dil Uni" of the container name of the reagent container 4 on "Name".

FIG. 12 is a view illustrating the display items of the Detail window 230B when the reagent loader 6 is automatically closed. In the example of FIG. 12, the status ("Status") of the reagent container 4 placed at the reagent loader 6 is "A. CLOSE". In the example of FIG. 12, the control unit 19a displays on "Name". Furthermore, when auto closing is performed in a state where the entire positions are empty, the control unit 19a changes the color of all areas 212a of the loader position display area 212 to the color meaning the empty positions.

FIG. 13 is a view illustrating the display item of the Detail window 230B when the reagent type is unknown. In the example of FIG. 13, the status ("Status") of the reagent container 4 placed at the reagent loader 6 is "UNKNOWN". In addition, in the example of FIG. 13, the control unit 19a displays on "Name".

In FIGS. 9 to 13, in the case of the reagent which already has the calibration information showing the information (measuring results) on calibration, the control unit 19a may display the measuring date and time on the Detail window 230B as the calibration information.

In addition, when the reagent accommodated in the reagent container 4 is linked with a preprocessing reagent accommodated in another reagent container 4, the control unit 19a may display the link information showing information on the linked preprocessing reagent on the Detail window 230B. However, when the type of the reagent accommodated in the reagent container 4 is "PRE", the control unit 19a displays the name of a test item instead of the link information.

Figure 14:
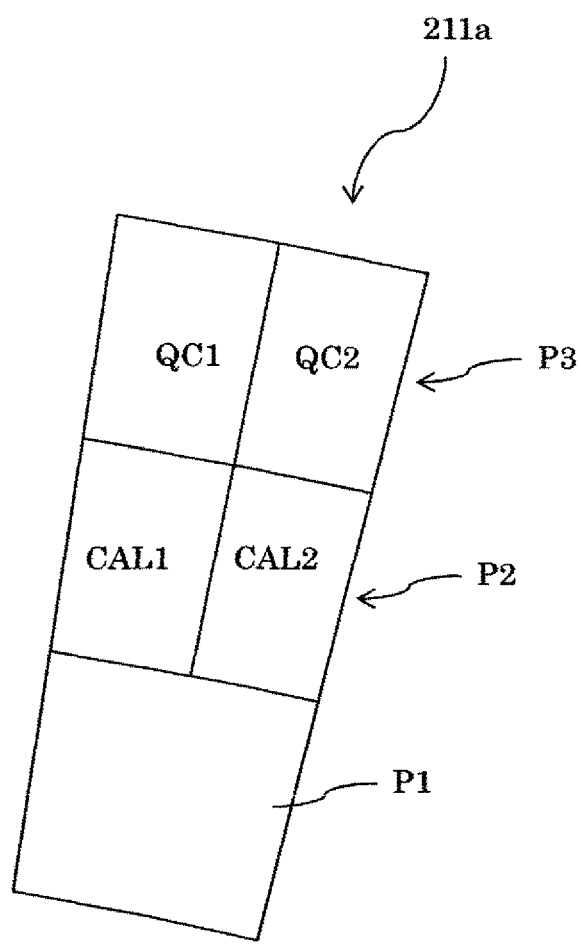
FIG. 14 is an enlarged view of the area 211a of the disc position display area illustrated in FIG. 4.

Next, the configuration of the area 211a of the disc position display area 211 will be described with reference to FIG. 14. FIG. 14 is an enlarged view of the area 211a of the disc position display area 211 illustrated in FIG. 4.

The area 211a is configured by third through fifth areas P1 to P3. In this case, the fourth area P2 is divided into a sixth area CAL1 and a seventh area CAL2. In addition, the fifth area P3 is divided into an eighth area QC1 and a ninth area QC2. In the embodiment, the control unit 19a changes the colors of respective areas constituting the area 211a in accordance with the status of the reagent container 4 corresponding to the area 211a.

In other words, the color of the area P1 shows the status of the reagent accommodated in the reagent container 4 corresponding to the area 211a. The colors of the area CAL1 and area CAL2 respectively show calibration results of the first and second channels in relation to the reagent accommodated in the reagent container 4 corresponding to the area 211a. The area QC1 and the area QC2 respectively show information management measuring results of the first and second channels in relation to the reagent accommodated in the reagent container 4 corresponding to the area 211a. Furthermore, the calibration and the information management measuring are performed by a first measuring system (the channel 1) and a second measuring system (the channel 2).

In this case, the control unit 19a changes the display state of the area P1 on the basis of whether the reagent container 4 is placed at a position on the reagent disc 5 corresponding to the area 211a and the reagent information of the reagent accommodated in the placed reagent container 4. The control unit 19a changes the display state of the area CAL1 and area CAL2 on the basis of the calibration information measured by the first measuring system and the second measuring system in relation to the reagent accommodated in the reagent container 4 placed at a position on the reagent disc 5 corresponding to the area 211a. The control unit 19a changes the display state of the area QC1 and area QC2 on the basis of the control management measuring information measured by the first measuring system and the second measuring system in relation to the reagent accommodated in the reagent container 4 placed at a position on the reagent disc 5 corresponding to the area 211a.

Next, the meaning of the color used for the area 211a of the disc position display area 211 will be described with reference to FIG. 15. FIG. 15 is a view illustrating an example of colors used for the area 211a of the disc position display area 211.

As illustrated in FIG. 15, colors C1 to C8 of respective areas constituting the area 211a show the present state of the reagent accommodated in the reagent container 4 placed on the reagent disc 5. Furthermore, the empty position inside the reagent disc 5, a reagent container 4 that is no longer necessary, and the like are displayed by the status colors of the area 211a.

In other words, the control unit 19a changes the colors of respective areas constituting the area 211a on the basis of whether the reagent container 4 is placed at a position on the reagent disc 5 corresponding to the area 211a and the reagent information of the reagent accommodated in the placed reagent container 4.

In addition, the control unit 19a monitors whether the reagent container 4 storing a reagent of a required item is placed and shows a guide display when the reagent container 4 is not placed. The control unit 19a updates the display item at a predetermined period (for example, 60 seconds).

Next, the meaning of the color used for the area 212a of the loader position display area 212 will be described with reference to FIG. 16. FIG. 16 is a view illustrating an example of the color used for the area 212a of the loader position display area 212. In addition, the control unit 19a turns on an LED of the color corresponding to the state of the reagent container 4 placed at the slot of the reagent loader 6. The LED is provided in the automatic analyzer 100 for each slot of the reagent loader 6. It is preferable that colors C2 to C6 used for the area 212a of the loader position display area 212 be matched to LED colors C11 to C14 as much as possible.

As illustrated in FIG. 16, the status color of the area 212a of the loader position display area 212 shows the present state of the reagent accommodated in the reagent container 4 placed on the reagent loader 6. Furthermore, the empty position in the reagent loader 6, the reagent container 4 which is placed at the reagent loader 6 and is in the middle of carrying into the reagent disc 5, the reagent container 4 which is placed at the reagent disc 5 and is in the middle of carrying-out from the reagent disc 5, the reagent container 4 which is temporarily stored by auto-closing, and the reagent container 4 which is in the middle of carrying-out from the reagent disc 5 by being specified by a user are displayed by the status colors.

In other words, the control unit 19a changes the display state of the area 212a on the basis of whether the reagent container 4 is placed at a position on the reagent loader 6 corresponding to the area 212a and conveyance-state information showing the conveyance state of the placed reagent container 4. In addition, the control unit 19a changes the display state of the area 212a on the basis of reagent information of the reagent accommodated in the reagent container 4 placed at a position on the reagent loader 6 corresponding to the area 212a.

The reagent container 4 placed at the reagent loader 6 includes a reagent container 4 to be carried into the reagent disc 5, the container being directly placed at the slot of the reagent loader 6 by a user, a reagent container 4 which is ordered to be taken out through the input unit 19c by a user, a reagent container 4 which is determined by the control unit 19a as an unavailable container and is automatically sent to the slot of the reagent loader 6, and the like.

When the reagent container 4 is sent to the reagent loader 6 from the reagent disc 5, the scanning device scans the individual identification mark 4d adhered to the reagent container 4. The control unit 19a recognizes that the reagent container 4 is placed at the slot of the reagent loader 6 and changes the screen display of the area 212a for each slot of the reagent loader 6 on the basis of the signals output from the scanning device.

For example, when the reagent accommodated in the reagent container 4 placed at a position on the reagent loader 6 is in a temporarily unavailable state and the conveyance state of the reagent container 4 is the carrying-out state, the control unit 19a changes the display state of the area 212a. The temporarily unavailable state is, for example, a case where the Foam/Film of a reagent is detected. When the reagent accommodated in the reagent container 4 placed at a position on the reagent loader 6 is in a permanently unavailable state due to the expired date or the like and the conveyance state of the reagent container 4 is in a carrying-out state, the control unit 19a changes the display state of the area 212a.

In addition, when the reagent container 4 placed at the reagent loader 6 is temporarily conveyed into the reagent disc 5 by auto-closing, the control unit 19a changes the display state of the area 212a. When there is no location in the reagent disc 5 at which the reagent container 4 is placed (when there is no empty position), the control unit 19a changes the display state of the area 212a.

The disc position display area 211 showing the status of the reagent container 4 placed at the reagent disc 5 and the loader position display area 212 showing the status of the reagent container 4 placed at the slot of the reagent loader 6 are displayed on a single Reagent window 210, and thus it is easy for a user to appropriately determine the time for exchanging a reagent.

For example, when the reagent containers 4 to be carried out are placed at only a part of the slots of the reagent loader 6 and there are no special hurry circumstances, it is possible to prevent a change in the temperature inside the reagent disc 5 when the conveyance processing of the reagent container 4 by the reagent loader 6 is not performed and stands by.

On the contrary, when the reagent containers 4 to be carried out are placed at all slots of the reagent loader 6, it is preferable that a user instructs the carrying-out processing by the reagent loader 6. Generally, when many reagent containers 4 to be carried out are placed at the slots of the reagent loader 6, it is not necessary to lift the reagent loader 6 several times for carrying out reagent vessels, and thus the time required for taking out reagents or exchanging reagents is reduced and it is possible to minimize the change in the temperature inside a reagent storage.

Furthermore, the disc position display area 211 showing the state of the reagent container 4 placed at the reagent disc 5 is also displayed, in such a manner that a user can check the state where many reagent containers 4 to be carried out stand by in the reagent disc 5 by a single screen. When many reagent containers 4 to be carried out stand by, it is necessary to repeatedly lift the reagent loader 6, and thus it is expected that it take a long time to carry out the reagent containers 4.

According to this embodiment, a user can expect whether a relatively long time is taken to the carrying-in/carrying-out operation of the reagent container 4 in advance, and thus the device can be smoothly operated even by a user who is busy with managing a plurality of various devices.

The control unit 19a displays the temperature inside the reagent disc 5 on the temperature displaying area 213 of the Reagent window 210. In this case, when the temperature inside the reagent disc 5 is equal to or greater than a predetermined temperature, the control unit 19a changes the display color of the temperature displaying area 213.

An opening portion can be provided in the reagent disc 5 by the operation of the reagent loader 6, and thus the temperature inside the reagent disc 5 changes. It is necessary to keep the reagents, being used for the automatic analyzer 100, cold at a constant temperature and deterioration of the reagent occurs by a change in the temperature. It is possible to attract attention related to the frequency of use of the reagent loader 6 by displaying the temperature inside the reagent disc 5 with the state of the reagent container 4 placed at the reagent loader 6.

According to this embodiment, it is possible to effectively perform the exchange of reagents using a reagent loader, as described above. In detail, the usability for reagent exchange can be improved in the automatic analyzer 100 by displaying the disc position display area 211 showing the state of the reagent container 4 placed at the reagent disc 5 and the loader position display area 212 showing the state of the reagent container 4 placed at the reagent loader 6 on the same screen.

Further, the invention is not limited to the embodiment described above and includes various embodiments. The embodiment described above is for clarity of the description of the invention and is not necessarily limited to those having all configurations described above. In addition, a part of the configuration of one embodiment can be replaced with the configuration of the other embodiment and the configuration of one embodiment can be added to the other configuration of the embodiment. Furthermore, adding/removing/replacing of the other configuration can be performed on a part of the configuration of each embodiment.

In the embodiment described above, the statuses of reagents accommodated in the reagent containers 4 placed at positions corresponding to respective areas are displayed by the color of the area 211a and the area 212a. However, it is not limited to the color-coded display because it is enough as long as each status can be identified on a screen. Patterns or marks may be given to respective reagent mounting positions or light may flash.

REFERENCE SIGNS LIST 1 sample container
2 sample container rack
3 rack conveyance line
4 reagent container (rack pack)
4a, 4b, 4c reagent vessel
4d individual identification mark
5 reagent disc (reagent container storage portion)
6 reagent loader
7 reagent disc cover
7a reagent disc cover opening portion
8 reaction container
9 incubator disc
10 sample dispensing nozzle
11 reagent dispensing nozzle
12 reaction container-sample dispensing chip accommodation portion
13 reaction container-sample dispensing chip accommodation portion
14 reaction container agitating mechanism
15 waste hole
16 conveyance mechanism
16a chip mounting position
17a, 17b nozzle
18a, 18b detection unit
19 control device
19a control unit (processor)
19d memory unit
100 automatic analyzer
200 screen
210 Reagent window
220 Inventory window
230 Detail window

The invention claimed is:

1. An automatic analyzer, comprising:
a reagent container storage portion which stores a plurality of reagent containers at a plurality of physical positions thereon;
a reagent loader which has a plurality of physical slots into which reagent containers are inserted and is configured to convey inserted reagent containers from outside the reagent container storage portion into the reagent container storage portion and convey reagent containers from inside the reagent container storage portion to the outside of the reagent container storage portion;
a memory unit storing reagent information indicating information of respective reagents accommodated in the plurality of reagent containers and conveyance-state information indicating information of respective conveyance states of the inserted reagent containers conveyed by the reagent loader, the reagent information including calibration information indicating respective calibration states of the reagents accommodated in the plurality of reagent containers stored on the reagent container storage portion;

a detection unit configured to detect a component of a reaction solution, including one of the respective reagents and a sample, in a reaction container;

a display unit; and a control unit connected to the reagent container storage portion, the reagent loader, the memory unit, the detection unit and the display unit, and programmed to control operations thereof, wherein the control unit is further programmed to:

display simultaneously, on a single screen of the display unit, a first display area including a first area, which corresponds to and is a graphical representation of a first position of the plurality of physical positions of the reagent container storage portion and a second display area including a second area, which corresponds to and is a graphical representation of a first slot of the plurality of physical slots of the reagent loader, when a first reagent container, of the plurality of reagent containers, is placed at the first position, change a display state of the first area to indicate that the first reagent container is placed at the first position corresponding to the first area and to indicate the reagent information of the reagent accommodated in the first reagent container placed at the first position, and when a second reagent container, of the plurality of reagent containers, is inserted at the first slot, change a display state of the second area to indicate that the second reagent container is inserted at the first slot corresponding to the second area and to indicate the conveyance-state information of the second reagent container inserted at the first slot, wherein the conveyance-state information of the second reagent container is one of a loading state, which is the second reagent container inserted at the first slot is being conveyed into the reagent container storage portion, and an unloading state, which is the second reagent container inserted at the first slot is being conveyed out from the reagent container storage portion, wherein the first area includes, within the graphical representation of the first position of the reagent container storage portion, a third area and a fourth area, wherein the control unit is further programmed to:

when the first reagent container is placed at the first position, change a display state of the third area to indicate that the first reagent container is placed at the first position corresponding to the first area, and when the first reagent container is placed at the first position, change a display state of the fourth area to indicate the calibration information of the accommodated reagent placed at the first position corresponding to the first area.

2. The automatic analyzer according to claim 1, wherein the control unit is further programmed to:

change the display state of the second area on the basis of the reagent information of the respective reagent accommodated in the second reagent container inserted at the first slot on the reagent loader corresponding to the second area.

3. The automatic analyzer according to claim 2, wherein the control unit is further programmed to:

when the second reagent container is inserted at the first slot and the second reagent container is being removed from the reagent loader, change the display state of the second area to indicate the second reagent container is in a temporarily unavailable state.

4. The automatic analyzer according to claim 2, wherein the control unit is further programmed to:

when the second reagent container is inserted at the first slot and the second reagent container is being removed from the reagent loader, change the display state of the second area to indicate the second reagent container is in a permanently unavailable state.

5. The automatic analyzer according to claim 2, wherein the control unit is further programmed to:

control the reagent loader to carry the second reagent container inserted at the first slot into the reagent container storage portion after a predetermined time is elapsed from when the second reagent container is inserted into the first slot from the outside, and when the reagent container placed at the reagent loader is carried into the reagent container storage portion from the outside, change the display state of the second area to indicate that the second reagent container is being carried by the reagent loader into the reagent container storage portion.

6. The automatic analyzer according to claim 1, wherein the control unit is further programmed to:

when there is no empty position among the plurality of positions in the reagent container storage portion, change the display state of the second area to indicate there is no empty position in the reagent container storage portion.

7. The automatic analyzer according to claim 1, further comprising:

a temperature sensor which measures a temperature inside the reagent container storage portion, wherein the single screen further includes a third display area, and the control unit is further programmed to:

display the temperature inside the reagent container storage portion measured by the temperature sensor in the third display area.

8. The automatic analyzer according to claim 7, wherein the control unit is further programmed to:

when the temperature inside the reagent container storage portion measured by the temperature sensor is equal to or greater than a predetermined threshold, change the display state of the third display area to indicate the temperature is equal to or greater than a predetermined threshold.

9. The automatic analyzer according to claim 1, wherein the first area includes, within the graphical representation of the first position of the reagent container storage portion, the third area, the fourth area, and a fifth area, the fourth area including a sixth area and a seventh area, and the fifth area including an eight area and a ninth area, and wherein the reagent information further includes control management measuring information indicating respective measurement states of the reagents accommodated in the plurality of reagent containers stored on the reagent container storage portion, and wherein the control unit is further programmed to:

change the display state of the sixth area to indicate the calibration information of the accommodated reagent placed at the first position corresponding to the first area measured by a first measuring system and the seventh area to indicate the calibration information of the accommodated reagent placed at the first position corresponding to the first area measured by a second measuring system, and change the display state of the eighth area to indicate the control management measuring information of the accommodated reagent placed at the first position corresponding to the first area measured by the first measuring system and the seventh area to indicate the control management measuring information of the accommodated reagent placed at the first position corresponding to the first area measured by the second measuring system.

10. The automatic analyzer according to claim 1, further comprising:

an input unit configured to select the first area or the second area, wherein the control unit is further programmed to:

change the display state of the first area in response to selecting the first area with the input unit, and change the display state of the second area in response to selecting the second area with the input unit.

11. The automatic analyzer according to claim 1, wherein the control unit is programmed to:

change the display state of the first area and the second area by changing respective colors of the first and second areas.

* * * * *